United States Patent [19]
Feit et al.

[11] 3,950,380
[45] Apr. 13, 1976

[54] PHENYL-BENZOIC ACID DERIVATIVES

[75] Inventors: Peter Werner Feit, Gentofte; Ole Bent Tvaermose Nielsen, Vanlose; Herta Bruun, Graested, all of Denmark

[73] Assignee: Leo Pharmaceutical Products Ltd. A/S, Ballerup, Denmark

[22] Filed: Aug. 20, 1974

[21] Appl. No.: 499,042

[30] Foreign Application Priority Data
Sept. 6, 1973 United Kingdom............... 42050/73

[52] U.S. Cl. ...... 260/465 D; 260/470; 260/294.8 F; 260/306.8 R; 260/309; 260/329 S; 260/347.2; 260/515 R
[51] Int. Cl.² ............... C07C 121/64; C07C 149/32; C07C 101/48; C07C 65/14
[58] Field of Search............ 260/518 R, 465 D, 470, 260/520

[56] References Cited
UNITED STATES PATENTS
3,816,482   6/1974   Feit et al. .......................... 260/518 R
3,872,167   3/1975   Hamprecht et al. ............. 260/518 R

*Primary Examiner*—Sam Rosen
*Attorney, Agent, or Firm*—Cushman, Darby & Cushman

[57] ABSTRACT

The present invention relates to a series of new compounds, their salts and esters and to methods for the preparation of the compounds having the general formula:

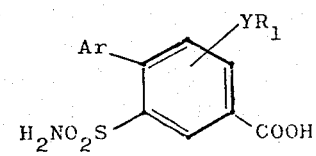

I in which $R_1$ represents a straight or branched $C_1$-$C_6$ alkyl, alkenyl or alkynyl radical, or a $C_1$-$C_3$ alkyl radical substituted with phenyl, halophenyl, trifluoromethylphenyl, (lower alkoxy)phenyl, or with a 5-membered or 6-membered heterocyclic ring containing not more than two heteroatoms selected from the group consisting of oxygen, sulphur and nitrogen; Ar stands for a phenyl radical, optionally being substituted with halogen, lower alkyl, hydroxy, or lower alkoxy; Y stands for O, S, NH or a $CH_2$ radical; and $YR_1$ is placed in the 2- or 3-position.

The compounds of the invention which are valuable in the human and veterinary practice, possess a pronounced diuretic and/or saluretic activity.

8 Claims, No Drawings

PHENYL-BENZOIC ACID DERIVATIVES

This invention relates to a series of new compounds, their salts and esters, said compounds having the general formula:

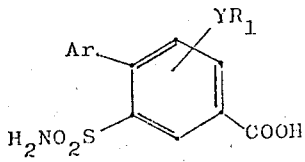

in which $R_1$ represents a straight or branched $C_1-C_6$ alkyl, alkenyl or alkynyl radical, or a $C_1-C_3$ alkyl radical substituted with phenyl, halophenyl, trifluoromethylphenyl, (lower alkoxy)phenyl, or with a 5-membered or 6-membered heterocyclic ring containing not more than two heteroatoms selected from the group consisting of oxygen, sulphur and nitrogen; Ar stands for a phenyl radical, optionally being substituted with halogen, lower alkyl, hydroxy, or lower alkoxy; Y stands for O, S, NH or a $CH_2$ radical; and $YR_1$ is placed in the 2- or 3-position.

In particular, $R_1$ may represent e.g. a methyl, ethyl, propyl, isopropyl, butyl, isobutyl or tert. butyl radical, or one of the different isomeric pentyl, or hexyl radicals, an alkenyl or alkynyl radical, e.g. on allyl, or propargyl radical, a benzyl or phenethyl radical, a 2-, 3-, or 4-pyridylmethyl, 2- or 3-furylmethyl, 2- or 3-thienylmethyl, thiazolylmethyl, or imidazolylmethyl radical; or one of the corresponding ethyl radicals.

Of particular value are the compounds in which $R_1$ is selected from the group consisting of straight or branched $C_3-C_3$ alkyl radicals, and a methyl radical being substituted with phenyl, furyl, thienyl, and pyridyl, and the correspondingly substituted ethyl radicals.

The substituents $R_1$ and Ar of formula I can be further substituted in different positions with different groups, such as one or more halogen atoms, e.g. chlorine or bromine atoms, lower alkyl, halo-lower alkyl, e.g. trifluoromethyl; amino groups, optionally being alkylated or acylated; hydroxy groups, which may be etherified, e.g. lower alkoxy, such as methoxy, ethoxy, n-propoxy, isopropoxy, n-butoxy or isobutoxy, or esterified with lower aliphatic carboxylic acids, such as lower alkanoic acids, e.g. acetic, propionic or pivalic acid, lower alkenoic acids, e.g. acrylic or methacrylic acid, or with lower aliphatic dicarboxylic dicarboxylic acids, e.g. oxalic, malonic, succinic, glutaric, adipic, maleic or fumaric acid or their acid esters with lower alkanols, e.g. methanol or ethanol; or etherified mercapto groups such as methylthio, ethylthio, isopropylthio, butylthio or isobutylthio radicals.

Whenever the expression "lower alkyl" is used in the foregoing and in the following it stands for a straight or branched alkyl radical with from 1 to 6 carbon atoms in the chain.

The salts of the compounds prepared according to the invention are pharmaceutically acceptable salts, and include, for example, alkali metal salts, alkaline earth metal salts, the ammonium salts, or amine salts formed, for instance, from mono-, di- or trialkanolamines or cyclic amines. The esters of the compounds are preferably derived from lower aliphatic alcohols, cyanomethanol and benzyl alcohol.

The compounds of the invention are derivatives of biphenyl and it has unexpectedly been found that these compounds possess an outstanding diuretic and saluretic activity with a very low excretion of potassium ions and a low toxicity which make the present compounds particularly valuable in human and/or veterinary practice.

The present compounds are effective after oral, enteral or parenteral administration, and are preferably prescribed in the form of tablets, pills, dragees, or capsules containing the free acid or salts thereof with atoxic bases, or the esters thereof, mixed with carriers and/or auxiliary agents.

Salts, which are soluble in water, may with advantage be administered by injection. The compounds of the invention are useful in the treatment of oedematous conditions e.g. cardiac, hepatic, renal, lung, and brain oedema, or oedematous conditions during pregnancy, and of pathological conditions which produce an abnormal retension of the electrolytes of the body, and in the treatment of hypertension.

The compounds prepared according to the invention or their salts or esters can be conveniently administered in a dosage unit as a pharmaceutical preparation containing from 0.2 mg to 50 mg of the active compound. The compounds of formula I are preferably administered in amounts from 0.5 mg to 10 mg. By the term "dosage unit" is meant a unitary, i.e. a single dose capable of being administered to a patient, and which may be readily handled and packed, remaining as a physically stable unit dose, comprising either the active material as such or in a mixture of it with a pharmaceutical carrier and auxiliary agents.

In the form of a dosage unit the compounds may be administered one or more times a day at appropriate intervals. The daily dose usually amounts to from 0.5 to 50 mg always depending, however, on the condition of the patients and according to the prescription of the medical practitioner.

In pharmaceutical compositions containing the said compounds, organic or inorganic, solid or liquid carriers suitable for oral, enteral, or parenteral administration can be used to make up the composition. Gelatin, lactose, starch, magnesium stearate, talc, vegetable and animal fats and oils, gum, polyalkylene glycol, or other known carriers for medicaments are all suitable as carriers.

In the pharmaceutical compositions, the proportion of therapeutically active material to carrier substances can vary between 0.5 percent and 90 percent.

The compositions may further contain other therapeutic compounds applied in the treatment of, for example oedemas and hypertension, besides the well-known auxiliary agents. Such other compounds may be, for instance, Veratrum- or Rauwolfia alkaloids, e.g. reserpine, rescinnamine or protoveratrine or synthetic hypotensive compounds, e.g. hydralazine, or other diuretics and saluretics, such as the well-known benzothiadiazines, e.g. hydroflumethiazide, bendroflumethiazide, and the like. Potassium-sparing diuretics, e.g. triamterene, may also be used in the preparation of the compositions. For some purposes it may be desirable to add small amounts of aldosterone antagonists, e.g. spironolactone.

It is another object of the invention to provide methods of preparing the present compounds.

In one embodiment the said compounds are prepared according to the following reaction scheme

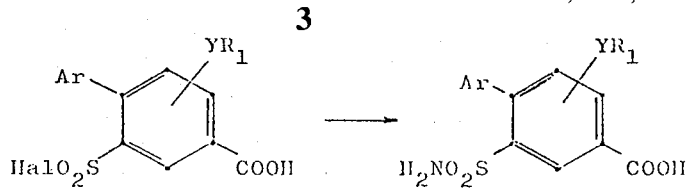

in which formulae the substituents $R_1$, Ar, and Y are as defined before, and Hal stands for a halogen atom, preferably chlorine. The compound of formula II is reacted with ammonia, preferably in the presence of a suitable solvent, such as water, or with a compound capable of liberating ammonia, such as ammonium salts or hexamethylenetetramine. The isolation of the compounds of formula I can be performed by means of well-known standard procedures.

When esters of the compounds of the formula II are used in the reaction, the compounds of the formula I are obtained as esters, or in some cases due to an aminolysis ass amides. The corresponding free acids may, optionally, be obtained by a subsequent saponification. In case of the desired product being an ester and the starting material of formula II being the free acid, as esterification can be performed either before or after the amidation process.

The starting compounds of formula II can e.g. be prepared from compounds of formula III

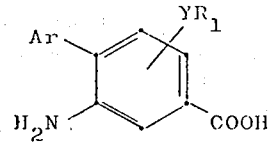

in which $R_1$, Ar and Y are as defined above. By subjecting these compounds to a diazotation followed by the well-known Meerwein-reaction, the corresponding 5-halosulfonyl derivatives of formula II are obtained.

The compounds of formula III can be prepared in different manners depending on the meaning and place of Y.

The starting materials of formula III in which $YR_1$ is placed in the 3-position are prepared from 3,5-dinitro-4-halobenzoic acid or preferably from an alkyl ester thereof which is subjected to an Ullmann reaction by reacting it with a substituted or unsubstituted halobenzene, preferably an iodobenzene or a bromobenzene in the presence of copper powder. Due to the high reactivity of the halogen atom between the two nitro groups the reaction can be performed at a rather moderate temperature giving high yields of the unsymmetric biphenyl derivative of the formula

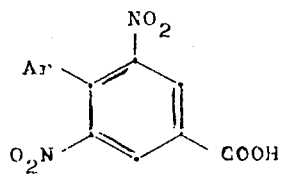

or an ester thereof.

A partial reduction of one of the nitro groups of the 4-Ar-3,5-dinitrobenzoic acid obtained by means of a reducing agent, such as an alkali dithionite, if necessary after saponification of the corresponding ester, yields the 3-amino-4-Ar-5-nitrobenzoic acid of the formula:

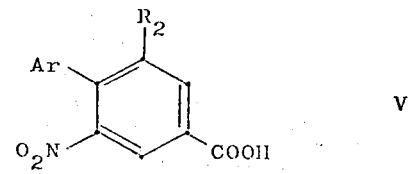

$R_2$ being an amino radical and Ar being as defined above.

The 3-amino group in compounds of formula V is diazotized, and the diazonium salt solution is heated, if necessary under acidic conditions, to give the corresponding 4-Ar-3-hydroxy-5-nitrobenzoic acid of formula V, $R_2$ being a hydroxy group. When the corresponding 3-mercapto derivative is desired, the above mentioned diazonium salt, if convenient after isolation and purification as e.g. a diazoniumtetrafluoroborate or a diazoniumchloride, is reacted with e.g. potassium ethyl xanthate or with potassium thiocyanate in the presence of copper thiocyanate or with an alkali disulfide followed by either a saponification or a reduction, dependent on the reactant used in the process. Thereby a compound of formula V, $R_2$ being a mercapto group, is obtained.

In a next step the compound of formula V, $R_2$ being an amino, a hydroxy or a mercapto group, is alkylated by treating the acid or one of its esters with a compound $R_1Z$, in which $R_1$ is as above defined and Z stands for a halogen atom, or an alkyl- or arylsulfonyloxy group or with a di-$R_1$-sulphate, a diazo compound of the formula $R_1N_2$, or a quaternary ammonium compound of the formula $R_1N^+(AlK)_3$, in which $R_1$ has the above meaning and AlK stands for alkyl with from 1 to 4 carbon atoms, resulting in a compound of formula VI

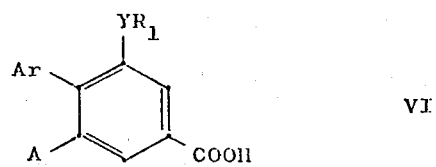

or an ester thereof, which can subsequently be saponified, and in which Y stands for NH, O, S; A is a $NO_2$ group, and in which $R_1$ and Ar have the above meanings.

For the preparation of the starting material of formula III in which Y stands for $CH_2$, the above mentioned diazonium salt prepared from a compound of formula V ($R_2 = NH_2$) is reacted with the appropriate alkene in known manner, the resulting 3-alkene-4-Ar- 5-nitrobenzoic acid thereafter being hydrogenated to the compound of the general formula VI in which A, depending on the reaction conditions used, is a nitro group, an amino group, or a group resulting from the formation of an intermediate during the reduction of A=NO₂ to A=NH₂, in which cases the compounds of formula VI represent the corresponding azo or hydrazo compounds.

When A is different from NH₂, the compounds of the formula VI are then reduced to compounds of formula III containing an amino group in the 5-position, for instance with an excess of sodium dithionite or with ferrous salts or iron powder or with stannous chloride.

The compounds of formula VI in which Y is oxygen or sulphur and A is a nitro group can be prepared by reacting the above mentioned diazonium salt prepared from a compound of formula V (R₂= NH₂) with a compound of the formula R₁YH, in which R₁ is as defined above and Y is oxygen or sulphur.

The starting materials of formula III in which YR₁ is placed in the 2-position are prepared from the well-known 2,4-dihalo-5-nitrotoluenes the methyl group of which is oxidized to a carboxylic group, whereafter the 2,4-dihalo-5-nitrobenzoic acid in which the halogen atoms may be the same of different is subjected to an Ullmann process as described above, whereby a compound of the formula IX is obtained:

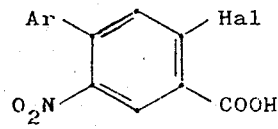

IX in which Ar is as defined above and Hal stands for a halogen atom. If desired, esters of the compounds can be used in the reactions, whereby also the compounds of formula IX are obtained as esters. If desired, a saponification can be preformed at any step of the preparation of the above and the following compounds. By reacting the compound of formula IX with a compound of the formula R₁Y'H in which Y' stands for O, S, or NH, preferably by heating and, if necessary, in the presence of an acid binding agent, in a suitable solvent or by using the reactant R₁Y'H as solvent, a compound of the following formula X is obtained:

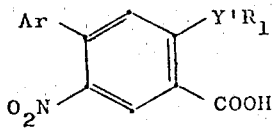

X in which Ar, Y' and R₁ all are as defined above.

By amination of the compound of formula IX the 2-amino-4-aryl-5-nitrobenzoic acid is formed, which latter compound through a diazotation and following reaction with an appropriate alkene in the manner described above, followed by a throughout hydrogenation yields a compound of the formula III, in which Y stands for CH₂.

In another embodiment the compound of formula IX can be reduced to the corresponding 5-amino derivative, which by following the method described above, can be diazotized, converted to the corresponding 5-halosulfonyl derivative which by amidation yields the 5-sulfamyl derivative of the formula XI:

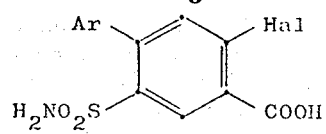

XI in which Ar and Hal are as defined above. By reacting this compound with the compound R₁Y'H as described above, compounds of formula I in which Y stands for O, S, or NH are obtained.

In another embodiment the compounds of formula I in which Y stands for oxygen, sulphur or methylene and is placed in the 3-position are prepared by reacting a diazonium salt of a compound of formula VII or an ester thereof

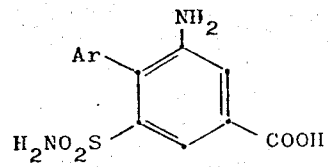

VII in which Ar is as defined above, with a compound of the formula R₁YH, in which R₁ is as defined above and Y stands for oxygen and sulphur, or with an appropriate alkene, in the latter case followed by hydrogenation of the alkene group thus introduced in the 3-position. These reactions are performed in the same manner as already described for the intermediates mentioned above.

The starting materials of formula VII are prepared by a Meerwein reaction on a compound of formula V, R₂=NH₂ and an amidation of the sulfochloride obtained, followed by a reduction of the nitro group to an amino group in known manner.

In another embodiment of the method the compounds of the invention in which Y stands for O, S or NH can be prepared from the compounds of the formula VIII

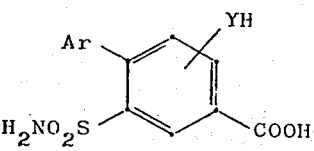

VIII in which Ar is as defined above by an alkylation. This can be performed either on the free acid or on one of its esters by treatment with a compound R₁Z in which R₁ has the meaning given above and Z stands for a halogen atom, or an alkyl- or arylsulfonyloxy group, or with a di-R₁-sulphate, a diazo compound of the formula R₁N₂, or a quaternary ammonium compound of the formula R₁N⁺(AlK)₃, in which R₁ has the above meaning and AlK stands for alkyl with from 1 to 6 carbon atoms.

In case of Y standing for NH, the alkylation may also be performed by a reductive alkylation using an aldehyde corresponding to R₁ in having the same carbon atom content.

The invention will now be illustrated by the following non-limiting Examples from which the details of the embodiments will be apparent.

EXAMPLE 1

3-Benzylamino-4-phenyl-5-sulfamylbenzoic acid

A. Methyl 3,5-dinitro-4-phenylbenzoate

A mixture of methyl 4-chloro-3,5-dinitrobenzoate (60 g), iodobenzene (36 ml) and copper powder (60 g) is stirred at 145°–155°C for 4-5 hours. After cooling, the resulting solids are extracted with three portions of boiling chloroform (each portion 150 ml), and the combined extracts are, after filtration, evaporated in vacuo. After trituration of the residue with methanol (150 ml) followed by recrystallization from 2-methoxyethanol, methyl 3,5-dinitro-4-phenylbenzoate is obtained with a melting point of 147.5°–148°C.

B. 3,5-Dinitro-4-phenylbenzoic acid

To a stirred suspension of methyl 3,5-dinitro-4-phenylbenzoate (145 g) in 2-methoxyethanol (1.5 l), 2 N sodium hydroxide (300 ml) is added dropwise during about 30 minutes. After additional stirring for about 15 minutes, the resulting solution is acidified by the dropwise addition of 4 N hydrochloric acid (250 ml), and the mixture is thereafter diluted with water (about 3 l). After cooling, the resulting precipitate is collected by filtration, washed with water and dried. After recrystallization from aqueous ethanol, 3,5-dinitro-4-phenylbenzoic acid is obtained with a melting point of 219°–221°C.

C. 3-Amino-5-nitro-4-phenylbenzoic acid

To a stirred solution of 3,5-dinitro-4-phenylbenzoic acid (135 g) in a mixture of pyridine (625 ml) and water (625 ml), sodium dithionite (235 g) is added in portions during about 30 minutes, keeping the temperature at 12°–15°C by external cooling. After additional stirring at this temperature for about 15 minutes, the resulting solution is acidified by the addition of conc. hydrochloric acid (750 ml), keeping the temperature below 25°C by the addition of ice to the reaction mixture. The mixture is left for about 20 hours, and the resulting precipitate is then collected by filtration, washed with water and dried. After recrystallization from aqueous ethanol, 3-amino-5-nitro-4-phenylbenzoic acid is obtained with a melting point of 247°–249°C (dec.).

D. 3-Benzylamino-5-nitro-4-phenylbenzoic acid

A mixture of 3-amino-5-nitro-4-phenylbenzoic acid (4.0 g), benzylbromide (4.0 ml), and ethanol (40 ml) is refluxed for 40 hours. After 16 and 24 hours additional amounts of benzylbromide (each portion 2.0 ml) are added. After cooling, the mixture is evaporated in vacuo and the obtained crude ethyl 3-benzylamino-5-nitro-4-phenylbenzoate is saponified by heating with a mixture of 2 N sodium hydroxide (25 ml) and ethanol (25 ml) for about 1 hour. The cooled mixture is acidified with acetic acid (5 ml) and diluted with water (15 ml). After cooling at about 5°C for 48 hours, the resulting precipitate is collected by filtration, washed with water and dried. After recrystallization from aqueous ethanol, 3-benzylamino-5-nitro-4-phenylbenzoic acid is obtained with a melting point of 188°–189°C.

E. 5-Amino-3-benzylamino-4-phenylbenzoic acid

To a stirred solution of 3-benzylamino-5-nitro-4-phenylbenzoic acid (3.0 g) in a mixture of pyridine (15 ml) and water (15 ml), sodium dithionite (6.0 g) is added in portions during about 15 minutes. The mixture is heated on a steam bath for about 30 minutes, and is then evaporated in vacuo. The residue is treated with cold 1 N acetic acid (about 50 ml) and after cooling, the resulting precipitate is collected by filtration, washed with water and dried. After recrystallization twice from aqueous ethanol, 5-amino-3-benzylamino-4-phenylbenzoic acid is obtained with a melting point of 179°–181°C.

F. 3-Benzylamino-5-chlorosulfonyl-4-phenylbenzoic acid

A solution of 5-amino-3-benzylamino-4-phenylbenzoic acid (0.65 g) and potassium nitrite (0.17 g) in 0.5 N potassium hydroxide (8 ml) is dropwise added to a mixture of acetic acid (7 ml) and conc. hydrochloric acid (7 ml), while stirring at 0°C. After additional stirring at this temperature for about 10 minutes, the resulting diazonium solution is added to a mixture of acetic acid (7 ml) saturated with SO₂ and cupric chloride dihydrate (0.2 g) in water (0.7 ml). After additional stirring for 2-3 hours, the precipitated 3-benzylamino-5-chlorosulfonyl-4-phenylbenzoic acid is collected by filtration, washed with water and dried.

G. 3-Benzylamino-4-phenyl-5-sulfamylbenzoic acid

3-Benzylamino-5-chlorosulfonyl-4-phenylbenzoic acid (1.0 g) is in portions added to conc. ammonium hydroxide (10 ml) while stirring at 10°–12°C. After additional stirring at room temperature for about 18 hours, the resulting solution is dropwise added to an excess of icecold 4 N hydrochloric acid. The resulting precipitate is collected by filtration, washed with water and dried. After recrystallization from aqueous ethanol, 3-benzylamino-4-phenyl-5-sulfamylbenzoic acid is obtained with a melting point of 221°–222°C.

EXAMPLE 2

3-Benzyloxy-4-phenyl-5-sulfamylbenzoic acid

A. 5-Carboxy-3-nitro-2-phenylbenzenediazonium tetrafluoroborate

A hot solution of 3-amino-5-nitro-4-phenylbenzoic acid (39 g; prepared as in Example 1, step C) and potassium nitrite (15 g) in 1 N potassium hydroxide (260 ml) is added dropwise to a mixture of acetic acid (150 ml) and conc. hydrochloric acid (150 ml), while stirring vigorously at -2° to 2°C. After additional stirring at this temperature for about 10 minutes, 50% hydrofluoroboric acid (100 ml) is added during about 5 minutes, keeping the temperature below 5°C by external cooling. After additional stirring at about -10°C for 1 hour, the precipitated 5-carboxy-3-nitro-2-phenylbenzenediazonium tetrafluoroborate is collected by filtration, washed with icecold water (two portions of each 25 ml) and dried.

B. 3-Hydroxy-5-nitro-4-phenylbenzoic acid

5-Carboxy-3-nitro-2phenylbenzenediazonium tetrafluoroborate (110 g) is added in portions to a stirred and refluxing mixture of acetic anhydride (275 ml) and acetic acid (275 ml). The mixture is refluxed for a further 4–5 hours and is then poured into ice-water (about 4 liters). The mixture is left for 20 hours, and the precipitated crude 3-acetoxy-5-nitro-4-phenylbenzoic acid is collected by filtration, washed with water and dried. It is saponified by heating with 4 N sodium hydroxide (250 ml) for 30 minutes; the resulting solution is left at 5°C for about 20 hours and is then filtered. The filtrate is acidified with 4 N hydrochloric acid to precipitate 3-hydroxy-5-nitro-4-phenylbenzoic acid. It is collected by filtration, washed with water and dried. After recrystallization from aqueous methanol, the acid is obtained with a melting point of 213°–215°C.

C. 3-Benzyloxy-5-nitro-4-phenylbenzoic acid

A mixture of 3-hydroxy-5-nitro-4-phenylbenzoic acid (3.0 g), benzylbromide (1.5 ml) and 1 N sodium hydroxide (30 ml) is stirred at room temperature for 6-7 hours. After cooling, the precipitated sodium 3-benzyloxy-5-nitro-4-phenylbenzoate is collected by filtration and washed with a small amount of icecold water. After drying, the sodium salt is dissolved in hot water (100 ml), and the 3-benzyloxy-5-nitro-4-phenylbenzoic acid is precipitated by addition of 4 N hydrochloric acid (10 ml). After cooling, the acid is collected by filtration, washed with water and dried. After recrystallization twice from isopropanol, it is obtained with a melting point of 188.5°–189.5°C.

D. 5-Amino-3-benzyloxy-4-phenylbenzoic acid

To a solution of 3-benzyloxy-5-nitro-4-phenylbenzoic acid (2.5 g) in a mixture of pyridine (8 ml) and water (16 ml), sodium dithionite (5.0 g) is added in portions during about 15 minutes. The mixture is heated on a steam bath for 30 minutes, and is then cooled in an ice-bath. The stirred and cooled mixtures is then acidified with 4 N hydrochloric acid to precipitate 5-amino-3-benzyloxy-4-phenylbenzoic acid. The acid is collected by filtration, washed with water and dried. After recrystallization from aqueous ethanol, it is obtained as a hemihydrate with a melting point of 161°–162°C.

E. 3-Benzyloxy-5-chlorosulfonyl-4-phenylbenzoic acid

By replacing in Example 1, step F, 5-amino-3-benzylamino-4-phenylbenzoic acid with an equimolar amount of 5-amino-3-benzyloxy-4-phenylbenzoic acid, and following the procedure described, 3-benzyloxy-5-chlorosulfonyl-4-phenylbenzoic acid is obtained.

F. 3-Benzyloxy-4-phenyl-5-sulfamylbenzoic acid

3-Benzyloxy-5-chlorosulfonyl-4-phenylbenzoic acid (1.0 g) is in portions added to conc. ammonium hydroxide (10 ml), while stirring at 10°–12°C. After additional stirring at room temperature for 18–20 hours, the mixture is left in a refrigerator for 2–3 hours. The separated ammonium salt is collected by filtration and washed with a small amount of icecold water. After drying, the salt is dissolved in 1 N sodium hydroxide (10 ml) and the 3-benzyloxy-4-phenyl-5-sulfamylbenzoic acid is precipitated by the dropwise addition of the solution to 1 N hydrochloric acid (12 ml). The acid is collected by filtration, washed with water and dried. After recrystallization from aqueous ethanol, it is obtained with a melting point of 199°–200°C.

EXAMPLE 3

3-Ethoxy-4-phenyl-5-sulfamylbenzoic acid

A. Ethyl 3-hydroxy-5-nitro-4-phenylbenzoate

A mixture of 3-hydroxy-5-nitro-4-phenylbenzoic acid (22 g; prepared as in Example 2, step B), conc. sulfuric acid (10 ml) and ethanol (400 ml) is refluxed for 20 hours. The resulting solution is concentrated in vacuo to about 100 ml and is then diluted with water (about 300 ml). The separated ethyl 3-hydroxy-5-nitro-4-phenylbenzoate is collected by filtration, washed with water and dried. After recrystallization from carbon tetrachloride, the ester is obtained with a melting point of 128°–130°C.

B. 3-Ethoxy-5-nitro-4-phenylbenzoic acid

To a solution of sodium ethanolate (prepared from 0.5 g of sodium) in dry ethanol (40 ml), ethyl 3-hydroxy-5-nitro-4-phenylbenzoate (4.4 g) is added followed by ethyl iodide (2.5 ml), and the resulting solution is refluxed for 20 hours. After about 6 hours an additional amount of sodium ethanolate (prepared from 0.25 g of sodiumn) in dry ethanol (10 ml) is added followed by ethyl iodide (1.3 ml). The mixture is evaporated in vacuo, 2 N sodium hydroxide (25 ml) is added to the residue, and the mixture is heated on a steam bath for 30 minutes to form a clear solution. On cooling, sodium 3-ethoxy-5-nitro-4-phenylbenzoate separates. It is collected by filtration, and washed with a small amount of icecold water. After drying, the sodium salt is dissolved in hot water (50 ml), and the 3-ethoxy-5-nitro-4-phenylbenzoic acid is precipitated by addition of 4 N hydrochloric acid (5 ml). After cooling, the acid is collected by filtration, washed with water and dried. After recrystallization from aqueous ethanol, it is obtained with a melting point of 174°–176°C.

C. 5-Amino-3-ethoxy-4-phenylbenzoic acid

By replacing in Example 2, step D, 3-benzyloxy-5-nitro-4-phenylbenzoic acid with 3-ethoxy-5-nitro-4-phenylbenzoic acid, and following the procedure described, 5-amino-3-ethoxy-4-phenylbenzoic acid is obtained with a melting point of 137.5°–138.5°C.

5-Chlorosulfonyl-3-ethoxy-4-phenylbenzoic acid

By replacing in Example 1, step F, 5-amino-3-benzylamino-4-phenylbenzoic acid with an equimolar amount of 5-amino-3-ethoxy-4-phenylbenzoic acid, and following the procedure described, 5-chlorosulfonyl-3-ethoxy-4-phenylbenzoic acid is obtained.

E. 3-Ethoxy-4-phenyl-5-sulfamylbenzoic acid

By replacing in Example 2, step F, 3-benzyloxy-5-chlorosulfonyl-4-phenylbenzoic acid with 5-chlorosulfonyl-3-ethoxy-4-phenylbenzoic acid, and following the procedure described, 3-ethoxy-4-phenyl-5-sulfamylbenzoic acid is obtained with a melting point of 149°–150°C.

EXAMPLE 4

4Phenyl-3-n-propoxy-5-sulfamylbenzoic acid

A. 5-Nitro-4-phenyl-3-n-propoxybenzoic acid

By replacing in Example 3, step B, ethyl iodide with an equimolar amount of n-propyl iodide, and following the procedure described, 5-nitro-4-phenyl-3-n-propoxybenzoic acid is obtained with a melting point of 142.5°–144°C.

B. 5-Amino-4-phenyl-3-n-propoxybenzoic acid

By replacing in Example 2, step D, 3-benzyloxy-5-nitro-4-phenylbenzoic acid with 5-nitro-4-phenyl-3-n-propoxybenzoic acid, and following the procedure described, 5-amino-4-phenyl-3-n-propoxybenzoic acid is obtained with a melting point of 101°–102°C.

C. 5-Chlorosulfonyl-4-phenyl-3-n-propoxybenzoic acid

By replacing in Example 1, step F, 5-amino-3-benzylamino-4-phenylbenzoic acid with an equimolar amount of 5-amino-4-phenyl-3-n-propoxybenzoic acid, and following the procedure described, 5-chlorosulfonyl-4-phenyl-3-n-propoxybenzoic acid is obtained.

D. 4-Phenyl-3-n-propoxy-5-sulfamylbenzoic acid

By replacing in Example 1, step G, 3-benzylamino-5-chlorosulfonyl-4-phenylbenzoic acid with 5-chlorosulfonyl-4-phenyl-3-n-propoxybenzoic acid, and following the procedure described, 4-phenyl-3-n-propoxy-5-sulfamylbenzoic acid is obtained with a melting point of 155°–157°C.

EXAMPLE 5

3-n-Butoxy-4-phenyl-5-sulfamylbenzoic acid

A. 3-n-Butoxy-5-nitro-4-phenylbenzoic acid

By replacing in Example 3, step B, ethyl iodide with an equimolar amount of n-butyl iodide, and following the procedure described, 3-n-butoxy-5-nitro-4-phenylbenzoic acid is obtained with a melting point of 133°–134°C.

B. 5-Amino-3-n-butoxy-4-phenylbenzoic acid

By replacing in Example 2, step D, 3-benzyloxy-5-nitro-4-phenylbenzoic acid with 3-n-butoxy-5-nitro-4-phenylbenzoic acid, and following the procedure described, 5-amino-3-n-butoxy-4-phenylbenzoic acid is obtained with a melting point of 122°–124°C.

C. 3-n-Butoxy-5-chlorosulfonyl-4-phenylbenzoic acid

By replacing in Example 1, step F, 5-amino-3-benzylamino-4-phenylbenzoic acid with an equimolar amount of 5-amino-3-n-butoxy-4-phenylbenzoic acid, and following the procedure described, 3-n-butoxy-5-chlorosulfonyl-4-phenylbenzoic acid is obtained.

D. 3-n-Butoxy-4-phenyl-5-sulfamylbenzoic acid

By replacing in Example 1, step G, 3-benzylamino-5-chlorosulfonyl-4-phenylbenzoic acid with 3-n-butoxy-5-chlorosulfonyl-4-phenylbenzoic acid, and following the procedure described, 3-n-butoxy-4-phenyl-5-sulfamylbenzoic acid is obtained crystallizing with 0.25 mole of water with a melting point of 129°–131°C.

EXAMPLE 6

3-n-Pentyloxy-4-phenyl-5-sulfamylbenzoic acid

A. 5-Nitro-3-n-pentyloxy-4-phenylbenzoic acid

By replacing in Example 3, step B, ethyl iodide with an equimolar amount of n-pentyl iodide, and following the procedure described, 5-nitro-3-n-pentyloxy-4-phenylbenzoic acid is obtained with a melting point of 144°–146°C.

B. 5-Amino-3-n-pentyloxy-4-phenylbenzoic acid

By replacing in Example 2, step D, 3-benzyloxy-5-nitro-4-phenylbenzoic acid with 5-nitro-3-n-pentyloxy-4-phenylbenzoic acid, and following the procedure described, 5-amino-3-n-pentyloxy-4-phenylbenzoic acid is obtained crystallizing with 0.25 mole of water with a melting point of 134°–135°C.

C. 5-Chlorosulfonyl-3-n-pentyloxy-4-phenylbenzoic acid

By replacing in Example 1, step F, 5-amino-3-benzylamino-4-phenylbenzoic acid with an equimolar amount of 5-amino-3-n-pentyloxy-4-phenylbenzoic acid, and following the procedure described, 5-chlorosulfonyl-3-n-pentyloxy-4-phenylbenzoic acid is obtained.

D. 3-n-Pentyloxy-4-phenyl-5-sulfamylbenzoic acid

By replacing in Example 2, step F, 3-benzyloxy-5-chlorosulfonyl-4-phenylbenzoic acid with 5-chlorosulfonyl-3-n-pentyloxy-4-phenylbenzoic acid, and following the procedure described, 3-n-pentyloxy-4-phenyl-5-sulfamylbenzoic acid is obtained with a melting point of 152°–155°C.

EXAMPLE 7

4-Phenyl-3-propargyloxy-5-sulfamylbenzoic acid

A. 5-Nitro-4-phenyl-3-propargyloxybenzoic acid

By replacing in Example 3, step B, ethyl iodide with an equimolar amount of propargyl bromide, and following the procedure described, 5-nitro-4-phenyl-3-propargyloxybenzoic acid is obtained with a melting point of 145°–147°C.

B. 5-Amino-4-phenyl-3-propargyloxybenzoic acid

By replacing in Example 2, step D, 3-benzyloxy-5-nitro-4-phenylbenzoic acid with 5-nitro-4-phenyl-3-propargyloxybenzoic acid, and following the procedure described, 5-amino-4-phenyl-3-propargyloxybenzoic acid is obtained with a melting point of 172°–173°C.

C. 5-Chlorosulfonyl-4-phenyl-3-propargyloxybenzoic acid

By replacing in Example 1, step F, 5-amino-3-benzylamino-4-phenylbenzoic acid with an equimolar amount of 5-amino-4-phenyl-3-propargyloxybenzoic acid, and following the procedure described, 5-chlorosulfonyl-4-phenyl-3-propargyloxybenzoic acid is obtained.

D. 4-Phenyl-3-propargyloxy-5-sulfamylbenzoic acid

By replacing in Example 1, step G, 3-benzylamino-5-chlorosulfonyl-4-phenylbenzoic acid with 5-chlorosulfonyl-4-phenyl-3-propargyloxybenzoic acid, and following the procedure described, 4-phenyl-3-propargyloxy-5-sulfamylbenzoic acid is obtained with a melting point of 154°–155°C.

EXAMPLE 8

3-(2-phenethoxy)-4-phenyl-5-sulfamylbenzoic acid

A. 5-Nitro-3-(2-phenethoxy)-4-phenylbenzoic acid

By replacing in Example 3, step B, ethyl iodide with an equimolar amount of 2-phenylethylbromide, and following the procedure described, 5-nitro-3-(2-phenethoxy)-4-phenylbenzoic acid is obtained with a melting point of 172°–173°C.

B. 5-Amino-3-(2-phenethoxy)-4-phenylbenzoic acid

By replacing in Example 2, step D, 3-benzyloxy-5-nitro-4-phenylbenzoic acid with 5-nitro-3-(2-phenethoxy)-4-phenylbenzoic acid, and following the procedure described, 5-amino-3-(2-phenethoxy)-4-phenylbenzoic acid is obtained with a melting point of 159°–160°C.

C. 5-Chlorosulfonyl-3-(2-phenethoxy)-4-phenylbenzoic acid

By replacing in Example 1, step F, 5-amino-3-benzylamino-4-phenylbenzoic acid with an equimolar amount of 5-amino-3-(2-phenethoxy)-4-phenylbenzoic acid and following the procedure described, 5-chlorosulfonyl-3-(2-phenethoxy)-4-phenylbenzoic acid is obtained.

D. 3-(2-Phenethoxy)-4-phenyl-5-sulfamylbenzoic acid

By replacing in Example 2, step F, 3-benzyloxy-5-chlorosulfonyl-4-phenylbenzoic acid with 5-chlorosulfonyl-3-(2-phenethoxy)-4-phenylbenzoic acid and following the procedure described, 3-(2-phenethoxy)-4-phenyl-5-sulfamylbenzoic acid is obtained, crystallizing with 0.25 mole of water with a melting point of 108°–110°C.

EXAMPLE 9

4-Phenyl-5-sulfamyl-3-(3-thenyloxy)benzoic acid

A. 5-Nitro-4-phenyl-3-(3-thenyloxy)benzoic acid

By replacing in Example 3, step B, ethyl iodide with an equimolar amount of 3-bromomethylthiophene, and following the procedure described, 5-nitro-4-phenyl-3-(3-thenyloxy)benzoic acid is obtained with a melting point of 184°–186°C.

B. 5-Amino-4-phenyl-3-(3-thenyloxy)benzoic acid

By replacing in Example 2, step D, 3-benzyloxy-5-nitro-4-phenylbenzoic acid with 5-nitro-4-phenyl-3-(3-thenyloxy)benzoic acid, and following the procedure described, 5-amino-4-phenyl-3-(3-thenyloxy)benzoic acid is obtained as a hemihydrate with a melting point of 139°–140°C.

C. 5-Chlorosulfonyl-4-phenyl-3-(3-thenyloxy)-benzoic acid

By replacing in Example 1, step F, 5-amino-3-benzylamino-4-phenylbenzoic acid with an equimolar amount of 5-amino-4-phenyl-3-(3-thenyloxy)benzoic acid, and following the procedure described, 5-chlorosulfonyl-4-phenyl-3-(3-thenyloxy)benzoic acid is obtained.

D. 4-Phenyl-5-sulfamyl-3-(3-thenyloxy)benzoic acid

By replacing in Example 1, step G, 3-benzylamino-5-chlorosulfonyl-4-phenylbenzoic acid with 5-chlorosulfonyl-4-phenyl-3-(3-thenyloxy)benzoic acid, and following the procedure described, 4-phenyl-5-sulfamyl-3-(3-thenyloxy)-benzoic acid is obtained with a melting point of 222°–223°C.

EXAMPLE 10

3-Benzylthio-4-phenyl-5-sulfamylbenzoic acid

A. Ethylxanthic acid 5-carboxy-3-nitro-2-phenylphenyl ester

5-Carboxy-3-nitro-2-phenylbenzenediazonium tetrafluoroborate (75 g; prepared as in Example 2, step A) is added in portions to a solution of potassium ethyl xanthate (24 g) in water (250 ml), while stirring at 65°–70°C. After additional stirring at this temperature for 30 minutes, the mixture is cooled, and 4 N hydrochloric acid (25 ml) is added followed by water (200 ml). The separated ethylxanthic acid 5-carboxy-3-nitro-2-phenylphenyl ester is collected by filtration, washed with water and dried.

B. 3-Benzylthio-5-nitro-4-phenylbenzoic acid

A mixture of ethylxanthic acid 5-carboxy-3-nitro-2-phenylphenyl ester (3.7 g) and 2 N sodium hydroxide (35 ml) is heated on a steam bath for 10 minutes, while nitrogen is bubled through the mixture. After cooling to about 40°C, benzyl bromide (2.0 ml) is added to the resulting solution, and the mixture is stirred for 4-5 hours in a nitrogen atmosphere. After cooling, the separated sodium 3-benzylthio-5-nitro-4-phenylbenzoate is collected by filtration, washed with a small amount of icecold water and dried. The sodium salt is dissolved in hot water, and the 3-benzylthio-5-nitro-4-phenylbenzoic acid is precipitated by acidification with 4N hydrochloric acid (5 ml). After cooling, the acid is collected by filtration, washed with water and dried. After recrystallization from aqueous ethanol, it is obtained with a melting point of 188°–189°C.

C. 5-Amino-3-benzylthio-4-phenylbenzoic acid

By replacing in Example 2, step D, 3-benzyloxy-5-nitro-4-phenylbenzoic acid with 3-benzylthio-5-nitro-4-phenylbenzoic acid, and following the procedure described, 5-amino-3-benzylthio-4-phenylbenzoic acid is obtained with a melting point of 173°–174°C.

D. 3-Benzylthio-5-chlorosulfonyl-4-phenylbenzoic acid

By replacing in Example 1, step F, 5-amino-3-benzylamino-4-phenylbenzoic acid with an equimolar amount of 5-amino-3-benzylthio-4-phenylbenzoic acid and following the procedure described, 3-benzylthio-5-chlorosulfonyl-4-phenylbenzoic acid is obtained.

E. 3-Benzylthio-4-phenyl-5-sulfamylbenzoic acid

By replacing in Example 2, step F, 3-benzyloxy-5-chlorosulfonyl-4-phenylbenzoic acid with 3-benzylthio-5-chlorosulfonyl-4-phenylbenzoic acid, and following the procedure described, 3-benzylthio-4-phenyl-5-sulfamylbenzoic acid is obtained as a hemihydrate with a melting point of 114°–120°C.

EXAMPLE 11

4-Phenyl-3-N-propylthio-5-sulfamylbenzoic acid

A. 5-Nitro-4-phenyl-3-n-propylthiobenzoic acid

By replacing in Example 10, step B, benzyl bromide with an equimolar amount of n-propyl iodide, and following the procedure described, 5-nitro-4-phenyl-3-n-propylthiobenzoic acid is obtained with a melting point of 178.5°–180°C.

B. 5-Amino-4-phenyl-3-n-propylthiobenzoic acid.

By replacing in Example 2, step D, 3-benzyloxy-5-nitro-4-phenylbenzoic acid with 5-nitro-4-phenyl-3-n-propylthiobenzoic acid, and following the procedure described, 5-amino-4-phenyl-3-n-propylthiobenzoic acid is obtained with a melting point of 190°–191°C.

C. 5-Chlorosulfonyl-4-phenyl-3-n-propylthiobenzoic acid

By replacing in Example 1, step F, 5-amino-3-benzylamino-4-phenylbenzoic acid with an equimolar amount of 5-amino-4-phenyl-3-n-propylthiobenzoic acid, and following the procedure described, 5-chlorosulfonyl-4-phenyl-3-n-propylthiobenzoic acid is obtained.

D. 4-Phenyl-3-n-propylthio-5-sulfamylbenzoic acid

By replacing in Example 1, step G, 3-benzylamino-5-chlorosulfonyl-4-phenylbenzoic acid with 5-chlorosulfonyl-4-phenyl-3-n-propylthiobenzoic acid and following the procedure described, 4-phenyl-3-n-propylthio-5-sulfamylbenzoic acid is obtained as a hydrate with a melting point of 85°–87°C.

EXAMPLE 12.

3-n-Butylthio-4-phenyl-5-sulfamylbenzoic acid

A. 3-n-Butylthio-5-nitro-4-phenylbenzoic acid

By replacing in Example 10, step B, benzyl bromide with an equimolar amount of n-butyl iodide, and following the procedure described, 3-n-butylthio-5-nitro-4-phenylbenzoic acid is obtained crystallizing with 0.67 mole of water with a melting point of 147°–148°C.

B. 5-Amino-3-n-butylthio-4-phenylbenzoic acid

By replacing in Example 2, step D, 3-benzyloxy-5-nitro-4-phenylbenzoic acid with 3-n-butylthio-5-nitro-4-phenylbenzoic acid, and following the procedure described, 5-amino-3-n-butylthio-4-phenylbenzoic acid is obtained with a melting point of 143°–144°C.

C. 3-n-Butylthio-5-chlorosulfonyl-4-phenylbenzoic acid

By replacing in Example 1, step F, 5-amino-3-benzylamino-4-phenylbenzoic acid with an equimolar amount of 5-amino-3-n-butylthio-4-phenylbenzoic acid, and following the procedure described, 3-n-butylthio-5-chlorosulfonyl-4-phenylbenzoic acid is obtained.

D. 3-n-Butylthio-4-phenyl-5-sulfamylbenzoic acid

By replacing in Example 1, step G, 3-benzylamino-5-chlorosulfonyl-4-phenylbenzoic acid with 3-n-butylthio-5-chlorosulfonyl-4-phenylbenzoic acid, and following the procedure described, 3-n-butylthio-4-phenyl-5-sulfamylbenzoic acid is obtained as a hydrate with a melting point of 75°–77°C.

EXAMPLE 13.

3-Isopentylthio-4-phenyl-5-sulfamylbenzoic acid

A. 3-Isopentylthio-5-nitro-4-phenylbenzoic acid.

By replacing in Example 10, step B, benzyl bromide with an equimolar amount of isopentyl iodide, and following the procedure described, 3-isopentylthio-5-nitro-4-phenylbenzoic acid is obtained with a melting point of 143°–144°C.

B. 5-Amino-3-isopentylthio-4-phenylbenzoic acid

By replacing in Example 2, step D, 3-benzyloxy-5-nitro-4-phenylbenzoic acid with 3-isopentylthio-5-nitro-4-phenylbenzoic acid, and following the procedure described, 5-amino-3-isopentylthio-4-phenylbenzoic acid is obtained crystallizing with 0.25 mole of water with a melting point of 124.5°–125.5°C.

C. 5-Chlorosulfonyl-3-isopentylthio-4-phenylbenzoic acid

By replacing in Example 1, step F, 5-amino-3-benzylamino-4-phenylbenzoic acid with an equimolar amount of 5-amino-3-isopentylthio-4-phenylbenzoic acid, and following the procedure described, 5-chlorosulfonyl-3-isopentylthio-4-phenylbenzoic acid is obtained.

D. 3-Isopentylthio-4-phenyl-5-sulfamylbenzoic acid

By replacing in Example 1, step G, 3-benzylamino-5-chlorosulfonyl-4-phenylbenzoic acid with 5-chlorosulfonyl-3-isopentylthio-4-phenylbenzoic acid, and following the procedure described, 3-isopentylthio-4-phenyl-5-sulfamylbenzoic acid is obtained crystallizing with 0.5 mole of ethanol with a melting point of 70°-74°C.

EXAMPLE 14

3-Allylthio-4-phenyl-5-sulfamylbenzoic acid

A. 3-Allylthio-5-nitro-4-phenylbenzoic acid

By replacing in Example 10, step B, benzyl bromide with an equimolar amount of allyl bromide, and following the procedure described, 3-allylthio-5-nitro-4-phenylbenzoic acid is obtained with a melting point of 152°-153.5°C.

B. 3-Allylthio-5-amino-4-phenylbenzoic acid.

By replacing in Example 2, step D, 3-benzyloxy-5-nitro-4-phenylbenzoic acid with 3-allylthio-5-nitro-4-phenylbenzoic acid, and following the procedure described, 3-allylthio-5-amino-4-phenylbenzoic acid is obtained with a melting point of 149.5°-150.5°C.

C. 3-Allylthio-5-chlorosulfonyl-4-phenylbenzoic acid

By replacing in Example 1, step F, 5-amino-3-benzylamino-4-phenylbenzoic acid with an equimolar amount of 3-allylthio-5-amino-4-phenylbenzoic acid, and following the procedure described, 3-allylthio-5-chlorosulfonyl-4-phenylbenzoic acid is obtained.

D. 3-Allylthio-4-phenyl-5-sulfamylbenzoic acid

By replacing in Example 1, step G, 3-benzylamino-5-chlorosulfonyl-4-phenylbenzoic acid with 3-allylthio-5-chlorosulfonyl-4-phenylbenzoic acid, and following the procedure described, 3-allylthio-4-phenyl-5-sulfamylbenzoic acid is obtained as a hydrate with a melting point of 78°-81°C.

EXAMPLE 15

3-Crotylthio-4-phenyl-5-sulfamylbenzoic acid

A. 3-Crotylthio-5-nitro-4-phenylbenzoic acid

By replacing in Example 10, step B, benzyl bromide with an equimolar amount of crotyl bromide, and following the procedure described, 3-crotylthio-5-nitro-4-phenylbenzoic acid is obtained with a melting point of 138.5°-140°C.

B. 5-Amino-3-crotylthio-4-phenylbenzoic acid

By replacing in Example 2, step D, 3-benzyloxy-5-nitro-4-phenylbenzoic acid with 3-crotylthio-5-nitro-4-phenylbenzoic acid, and following the procedure described, 5-amino-3-crotylthio-4-phenylbenzoic acid is obtained with a melting point of 102°-104°C.

C. 5-Chlorosulfonyl-3-crotylthio-4-phenylbenzoic acid

By replacing in Example 1, step F, 5-amino-3-benzylamino-4-phenylbenzoic acid with an equimolar amount of 5-amino-3-crotylthio-4-phenylbenzoic acid, and following the procedure described, 5-chlorosulfonyl-3-crotylthio-4-phenylbenzoic acid is obtained.

D. 3-Crotylthio-4-phenyl-5-sulfamylbenzoic acid

By replacing in Example 1, step G, 3-benzylamino-5-chlorosulfonyl-4-phenylbenzoic acid with 5-chlorosulfonyl-3-crotylthio-4-phenylbenzoic acid, and following the procedure described, 3-crotylthio-4-phenyl-5-sulfamylbenzoic acid is obtained crystallizing with 0.5 mole of ethanol with a melting point of 89°-91°C.

EXAMPLE 16

4-Phenyl-5-sulfamyl-3-(3-thenylthio)benzoic acid

A. 5-Nitro-4-phenyl-3-(3-thenylthio)benzoic acid

By replacing in Example 10, step B, benzyl bromide with an equimolar amount of 3-bromomethylthiophene, and following the procedure described, 5-nitro-4-phenyl-3-(3-thenylthio)benzoic acid is obtained crystallizing with 0.25 mole of water with a melting point of 159°-161° C.

B. 5-Amino-4-phenyl-3-(3-thenylthio)benzoic acid

By replacing in Example 2, step D, 3-benzyloxy-5-nitro-4-phenylbenzoic acid with 5-nitro-4-phenyl-3-(3-thenylthio)benzoic acid, and following the procedure described, 5-amino-4-phenyl-3-(3-thenylthio)benzoic acid is obtained with a melting point of 142°-145°C. (dec.).

C. 5-Chlorosulfonyl-4-phenyl-3-(3-thenylthio)benzoic acid

By replacing in Example 1, step F, 5-amino-3-benzylamino-4-phenylbenzoic acid with an equimolar amount of 5-amino-4-phenyl-3-(3-thenylthio)benzoic acid, and following the procedure described, 5-chlorosulfonyl-4-phenyl-3-(3-thenylthio)benzoic acid is obtained.

D. 4-Phenyl-5-sulfamyl-3-(3-thenylthio)benzoic acid

By replacing in Example 2, step F, 3-benzyloxy-5-chlorosulfonyl-4-phenylbenzoic acid with 5-chlorosulfonyl-4-phenyl-3-(3-thenylthio)benzoic acid, and following the procedure described, 4-phenyl-5-sulfamyl-3-(3-thenylthio)-benzoic acid is obtained as a hydrate with a melting point of 92°-94°C.

EXAMPLE 17

4-Phenyl-3-(2-pyridylmethylthio)-5-sulfamylbenzoic acid

A. 5-Nitro-4-phenyl-3-(2-pyridylmethylthio)benzoic acid

By replacing in Example 10, step B, benzyl bromide with an equimolar amount of 2-chloromethylpyridine hydrochloride, and following the procedure described, 5-nitro-4-phenyl-3-(2-pyridylmethylthio)benzoic acid is obtained as a hemihydrate with a melting point of 235°-237°C (dec.).

B. 5-Amino-4-phenyl-3-(2-pyridylmethylthio)benzoic acid

By replacing in Example 1, step E, 3-benzylamino-5-nitro-4-phenylbenzoic acid with 5-nitro-4-phenyl-3-(2-pyridylmethylthio)benzoic acid, and following the procedure described, 5-amino-4-phenyl-3-(2-pyridylmethylthio)-benzoic acid is obtained with a melting point of 210°-211°C.

C. 5-Chlorosulfonyl-4-phenyl-3-(2-pyridylmethylthio)-benzoic acid

By replacing in Example 1, step F, 5-amino-3-benzylamino-4-phenylbenzoic acid with an equimolar amount of 5-amino-4-phenyl-3-(2-pyridylmethylthio)-benzoic acid, and following the procedure described, 5-chlorosulfonyl-4-phenyl-3-(2-pyridylmethylthio)-benzoic acid is obtained.

D. 4-Phenyl-3-(2-pyridylmethylthio)-5-sulfamylbenzoic acid

By replacing in Example 2, step F, 3-benzyloxy-5-chlorosulfonyl-4-phenylbenzoic acid with 5-chlorosulfonyl-4-phenyl-3-(2-pyridylmethylthio)benzoic acid, and following the procedure described, 4-phenyl-3-(2-pyridylmethylthio)-5-sulfamylbenzoic acid is obtained as a hydrate with a melting point of 83°–86°C.

EXAMPLE 18

3-Benzylamino-4-phenyl-5-sulfamylbenzoic acid

A. 5-Chlorosulfonyl-3-nitro-4-phenylbenzoic acid

A hot solution of 3-amino-5-nitro-4-phenylbenzoic acid (7.8 g; prepared as in Example 1, step C) and potassium nitrite (3.0 g) in 1 N potassium hydroxide (50 ml) is added dropwise to a mixture of acetic acid (30 ml) and conc. hydrochloric acid (30 ml), while stirring vigorously at −2 to 2°C. After additional stirring at this temperature for 10 minutes, the resulting diazonium-solution is added to a mixture of acetic acid (50 ml) saturated with $SO_2$ and cupric chloride dihydrate (2.0 g) in water (4 ml). After additional stirring for 2–3 hours, the precipitated 5-chlorosulfonyl-3-nitro-4-phenylbenzoic acid is collected by filtration, washed with water and dried.

B. 3-Nitro-4-phenyl-5-sulfamylbenzoic acid

By replacing in Example 1, step G, 3-benzylamino-5-chlorosulfonyl-4-phenylbenzoic acid with 5-chlorosulfonyl-3-nitro-4-phenylbenzoic acid, and following the procedure described, 3-nitro-4-phenyl-5-sulfamylbenzoic acid is obtained as a hydrate with a melting point of 119°–121°C.

C. 3-Amino-4-phenyl-5-sulfamylbenzoic acid

To a solution of 3-nitro-4-phenyl-5-sulfamylbenzoic acid (8.5 g) in acetic acid (100 ml), palladium (10%) on carbon (1.5 g) is added, and the mixture is hydrogenated. After 2–2.5 hours the theoretical amount of hydrogen has been absorbed, and the hydrogen uptake has subsided. The catalyst is removed by filtration, and the filtrate is evaporated in vacuo. The residue is recrystallized from acetic acid to give 3-amino-4-phenyl-5-sulfamylbenzoic acid with a melting point of 232.5°–237°C.

D. 3-Benzylamino-4-phenyl-5-sulfamylbenzoic acid

By replacing in Example 1, step D, 3-amino-5-nitro-4-phenylbenzoic acid with an equimolar amount of 3-amino-4-phenyl-5-sulfamylbenzoic acid, and following the procedure described, 3-benzylamino-4-phenyl-5-sulfamylbenzoic acid is obtained with a melting point of 221°–222°C. The material is identical (IR, analysis) with the material prepared as in Example 1, step G.

EXAMPLE 19

3-n-Butylamino-4-phenyl-5-sulfamylbenzoic acid.

A solution of 3-amino-4-phenyl-5-sulfamylbenzoic acid (1.46 g) and n-butyl iodide (1.5 ml) in n-butanol (20 ml) is refluxed for 3–4 days under such conditions, that the water formed during the reaction is separated. After 12, 24, 36 and 48 hours, additional amounts of n-butyl iodide (each time 0.75 ml) are added. The resulting solution is evaporated in vacuo, and the obtained crude n-butyl 3-n-butylamino-4-phenyl-5-sulfamylbenzoate is saponified by heating with 2 N sodium hydroxide (20 ml) for 30 minutes. After cooling, the resulting solution is acidified with 4 N hydrochloric acid (12 ml) to precipitate 3-n-butylamino-4-phenyl-5-sulfamylbenzoic acid, which is collected by filtration, washed with water and dried. After recrystallization from aqueous ethanol, the acid is obtained with a melting point of 134°–136°C.

EXAMPLE 20

3-Allylamino-4-phenyl-5-sulfamylbenzoic acid.

By replacing in Example 1, step D, 3-amino-5-nitro-4-phenylbenzoic acid and benzyl bromide with equimolar amounts of 3-amino-4-phenyl-5-sulfamylbenzoic acid and allyl bromide respectively, and following the procedure described, 3-allylamino-4-phenyl-5-sulfamylbenzoic acid is obtained with a melting point of 169°–172.5°C.

EXAMPLE 21

3-Crotylamino-4-phenyl-5-sulfamylbenzoic acid

By replacing in Example 1, step D, 3-amino-5-nitro-4-phenylbenzoic acid and benzyl bromide with equimolar amounts of 3-amino-4-phenyl-5-sulfamylbenzoic acid and crotyl bromide respectively, and following the procedure described, 3-crotylamino-4-phenyl-5-sulfamylbenzoic acid is obtained with a melting point of 186°–187°C.

EXAMPLE 22

3-(2-Furylmethylamino)-4-phenyl-5-sulfamylbenzoic acid

To a solution of sodium methanolate (prepared from 0.12 g of sodium) in methanol (15 ml), 3-amino-4-phenyl-5-sulfamylbenzoic acid (1.46 g) is added followed by furfural (1.5 ml), and the resulting solution is refluxed for 20 hours. After cooling, sodium borohydride (1.5 g) is added in portions during about 1 hour, while stirring at 0°–5°C. After additional stirring at room temperature for 2 hours, the solvents are removed in vacuo. The residue is dissolved in water (25 ml) and crude 3-(2-furylmethylamino)-4-phenyl-5-sulfamylbenzoic acid is precipitated by acidification with acetic acid. The crude acid is dissolved in hot saturated sodium hydrogen carbonate (15 ml), and the solution is filtered hot in the presence of decolorizing carbon. On cooling, the sodium salt separates. It is collected by filtration, washed with a small amount of icecold water and dried. The sodium salt is dissolved in hot water, and pure 3-(2-furylmethylamino)-4-phenyl-5-sulfamyl benzoic acid is precipitated by acidification with acetic acid. The acid is collected by filtration and is, after drying, obtained as a hydrate with a melting point of 167°–169°C.

EXAMPLE 23

4-Phenyl-3-(4-pyridylethylamino)-5-sulfamylbenzoic acid

A solution of 3-amino-4-phenyl-5-sulfamylbenzoic acid (1.46 g), 4-vinylpyridine (1.0 ml) and acetic acid (0.5 ml) in methanol (7.5 ml) is refluxed for 5–6 hours. After cooling, the resulting solution is diluted with water (16 ml) to precipitate crude 4-phenyl-3-(4-pyridylethylamino)-5-sulfamylbenzoic acid, which is collected by filtration, washed with water and dried. After recrystallization twice from aqueous ethanol, the acid is obtained with a melting point of 216.5°–217.5°C.

EXAMPLE 24

3-Benzylthio-4-phenyl-5-sulfamylbenzoic acid.

A. Ethylxanthic acid 5-carboxy-2-phenyl-3-sulfamyl-phenyl ester

To a solution of 3-amino-4-phenyl-5-sulfamylbenzoic acid (1.46 g) in a mixture of acetic acid (10 ml) and conc. hydrochloride acid (5 ml), a solution of sodium nitrite (0.35 g) in water (3.5 ml) is added dropwise, while stirring at 0°–5°C. The resulting diazonium-solution is carefully added in small portions to a solution of potassium ethyl xanthate (1.05 g) and sodium hydrogen carbonate (15 g) in water, while stirring at 70°–75°C. When the nitrogen evolution has subsided, the resulting solution is cooled, and the ethylxanthic acid 5-carboxy-2-phenyl-3-sulfamylphenyl ester is precipitated by acidification with 4 N hydrochloric acid.

B. 3-Benzylthio-4-phenyl-5-sulfamylbenzoic acid

A mixture of ethylxanthic acid 5-carboxy-2-phenyl-3-sulfamylphenyl ester (2.0 g) and 2 N sodium hydroxide (20 ml) is heated on a steam bath for 1 hour, while nitrogen is bubbled through the mixture. After cooling, the resulting solution is acidified with 4 N hydrochloric acid (12 ml) to precipitate crude 3-mercapto-4-phenyl-5-sulfamylbenzoic acid, which is collected by filtration, washed with water and dried. The crude acid is in portions added to saturated sodium hydrogen carbonate (15 ml) followed by solid sodium hydrogen carbonate (1.0 g) and sodium dithionite (1.0 g). To the resulting solution, benzyl bromide (1.3 ml) is added, and the mixture is stirred at room temperature for 6–7 hours. After cooling, the precipitated sodium 3-benzylthio-4-phenyl-5-sulfamylbenzoate is collected by filtration, washed with a small amount of icecold water and dried. The sodium salt is dissolved in hot water, and the 3-benzylthio-4-phenyl-5-sulfamylbenzoic acid is precipitated by acidification with 4 N hydrochloric acid. The acid, is, after cooling, collected by filtration, washed with water and dried. After recrystallization from aqueous ethanol, it is obtained as a hemihydrate with a melting point of 116°–119°C. The material is identical (IR, analysis) with the material prepared as in Example 10, step E.

What we claim is:

1. A compound of the general formula Ia

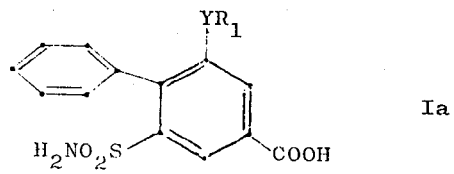

in which $R_1$ represents a straight or branched $C_1$-$C_6$ alkyl, alkenyl or alkynyl radical, benzyl or phenethyl; and Y stands for O, S, or NH; and pharmaceutically acceptable, non-toxic salts thereof; and esters thereof with cyano methanol, benzyl alcohol and $C_1$-$C_6$ alkanols.

2. A compound of formula Ia of claim 1, in which $R_1$ stands for a straight or branched $C_3$-$C_5$ alkyl radical, and Y has the meaning defined in claim 1.

3. 3-n-Butylthio-4-phenyl-5-sulfamylbenzoic acid and its salts and esters as defined in claim 1.

4. 3-Benzylthio-4-phenyl-5-sulfamylbenzoic acid and its salts and esters as defined in claim 1.

5. A compound of the general formula Ia

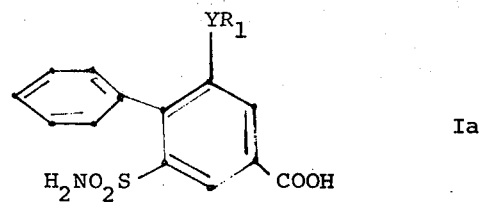

in which $R_1$ represents a straight or branched $C_1$-$C_6$ alkyl, alkenyl or alkynyl radical, benzyl or phenethyl; and Y stands for O or NH; and pharmaceutically acceptable, non-toxic salts thereof; and esters thereof with cyano methanol, benzyl alcohol and $C_1$-$C_6$ alkanols.

6. 3-Benzylamino-4-phenyl-5-sulfamylbenzoic acid and its salts and esters as defined in claim 5.

7. 3-n-Butoxy-4-phenyl-5-sulfamylbenzoic acid and its salts and esters as defined in claim 5.

8. 3-Benzyloxy-4-phenyl-5-sulfamylbenzoic acid and its salts and esters as defined in claim 5.

* * * * *